(12) United States Patent  
Nakano

(10) Patent No.: US 9,390,343 B2  
(45) Date of Patent: Jul. 12, 2016

(54) ESTIMATING DEGREE OF DETERIORATION OF ROAD SURFACE

(71) Applicant: International Business Machines Corporation, Armonk, NY (US)

(72) Inventor: Hiroki Nakano, Otsu (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/736,354

(22) Filed: Jun. 11, 2015

(65) Prior Publication Data

US 2016/0055392 A1  Feb. 25, 2016

(30) Foreign Application Priority Data

Aug. 19, 2014  (JP) .................... 2014-166736

(51) Int. Cl.
| | | |
|---|---|---|
| *G06K 9/34* | (2006.01) | |
| *G06K 9/46* | (2006.01) | |
| *G06T 7/00* | (2006.01) | |

(Continued)

(52) U.S. Cl.
CPC ............... *G06K 9/4633* (2013.01); *G01N 3/00* (2013.01); *G06K 9/481* (2013.01); *G06T 5/20* (2013.01); *G06T 7/0081* (2013.01); *G06T 7/0085* (2013.01); *G01N 2203/0062* (2013.01); *G06T 2207/20061* (2013.01); *G06T 2207/20192* (2013.01)

(58) Field of Classification Search
CPC ............ G01N 2203/0062; G01N 3/00; G06K 9/4633; G06K 9/481; G06T 2207/20061; G06T 2207/20192; G06T 5/20; G06T 7/0081; G06T 7/0085

See application file for complete search history.

(56) References Cited

U.S. PATENT DOCUMENTS

| | | | | |
|---|---|---|---|---|
| 6,983,065 B1* | 1/2006 | Akgul | .................. | G06K 9/4619 348/125 |
| 2012/0263342 A1* | 10/2012 | Haas | ........................ | G06K 9/00 382/100 |

FOREIGN PATENT DOCUMENTS

| | | |
|---|---|---|
| JP | 06-235626 A | 8/1994 |
| JP | 09-61138 A | 3/1997 |

(Continued)

OTHER PUBLICATIONS

JP patent application 2014-166736, entitled "Method and Algorithm for Estimating Degree of Deterioration of Road Surface (Crack Detection Technique Using Image Analysis by Applying Gabor Filter to Multiple Resolution Image," filed Aug. 19, 2014.

(Continued)

*Primary Examiner* — Phuoc Tran
(74) *Attorney, Agent, or Firm* — Scott A. Berger

(57) ABSTRACT

Image analysis methods for quantifying cracks in a road surface from a road surface image recorded as a digital image, and quantify the degree of deterioration of the road surface. An object image is prepared, in which its region is divided into a plurality of pixels and the grayscale value of each of the pixels is inverted. An image analysis technique may include, on the basis of an image obtained by applying a Gabor filter to a multiple resolution image, containing images with multiple scales obtained by scaling, cracks in a road surface can be detected and distinguished from white lines and characters on the road surface. It is possible to solve various problems, in which visually detected cracks do not appear as edges and edges of white lines and characters on the road surface are detected as line segment vectors.

20 Claims, 9 Drawing Sheets

(51) Int. Cl.
    *G06K 9/48*   (2006.01)
    *G06T 5/20*   (2006.01)
    *G01N 3/00*   (2006.01)

(56) References Cited

FOREIGN PATENT DOCUMENTS

| JP | 2000-285236 A | 10/2000 |
| JP | 2000-326494 A | 11/2000 |
| JP | 2004-145501 A | 5/2004 |
| JP | 2007-132858 A | 5/2007 |
| JP | 2007-155405 A | 6/2007 |
| JP | 2009-229085 A | 10/2009 |
| JP | 2010286995 A | 12/2010 |
| JP | 2011174794 A | 9/2011 |
| JP | 2011175468 A | 9/2011 |
| JP | 2011179874 A | 9/2011 |
| JP | 2011-242365 A | 12/2011 |
| JP | 2012098045 A | 5/2012 |
| JP | 2012194872 A | 10/2012 |

OTHER PUBLICATIONS

Konomi et al., "Crack Extraction from the Road Picture in Road Diagnostic Analysis," ITE Technical Report, The Institute of Image Information and Television Engineers, Feb. 10, 2014, vol. 38, No. 7, pp. 117-122, (English Abstract).

* cited by examiner

GABOR FILTER:

$$g(x, y; \lambda, \theta, \psi, \sigma, \gamma) = \exp\left(-\frac{x'^2 + \gamma^2 y'^2}{2\sigma^2}\right) \cos\left(2\pi \frac{x'}{\lambda} + \psi\right) \quad (1)$$

where
$x' = x \cos\theta + y \sin\theta$
$y' = -x \sin\theta + y \cos\theta$

EXAMPLE OF GABOR FILTER SHAPE ($\psi = 0$)

DISPLAYED AS GRAYSCALE IMAGE

EXAMPLE 2:
Image size = 500×500 pixels, $\sigma = 7.5$, $\lambda = 5\pi$, $\psi = \pi/2$

ESTIMATING DEGREE OF DETERIORATION OF ROAD SURFACE

BACKGROUND

The present disclosure relates to image analysis, and specifically relates to image analysis that quantifies cracks in a road surface to quantify the degree of deterioration of the road surface.

The deterioration of infrastructures, such as roads and bridges, caused by aging has been recognized as a problem in recent years. There has thus been a growing demand for regular monitoring and quantification of the degree of deterioration of such infrastructures.

In particular, since it is virtually impossible to quantify the surface condition of a long and wide highway through visual inspection, there is a need for automatic quantification through image analysis.

SUMMARY

Embodiments of the present disclosure provide for a method, system, and computer program product for image analysis that quantifies cracks in a road surface to quantify the degree of deterioration of the road surface.

One embodiment is directed toward a method for detecting cracks from an object image. The method includes dividing a region of the object image into a plurality of pixels. The method also includes inverting a grayscale value of each of the plurality of pixels. The method also includes preparing a group of filters with different rotational orientation components and applying one of the filters to the plurality of pixels. The method also includes setting values of pixels with filter responses greater than or equal to a first threshold value to 1 and setting values of the other pixels to 0. The method also includes applying a filter, to the plurality of pixels, wherein the filter responds to spatial frequencies of edges of white lines. The method also includes replacing a set value of a pixel with 0 if an absolute value of a filter response corresponding to the pixel is greater than or equal to a second threshold value and the set value of the pixel is 1. The method also includes extracting a line segment vector estimated to correspond to a crack by using a transform that estimates continuity of the plurality of pixels.

Another embodiment is directed toward a system for detecting cracks from an object image by being executed on a computer. The system performing the operations of dividing a region of the object image into a plurality of pixels. The system also performs the operation of inverting a grayscale value of each of the plurality of pixels. The system also performs the operation of preparing a group of filters with different rotational orientation components and applying one of the filters to the plurality of pixels. The system also performs the operation of setting values of pixels with filter responses greater than or equal to a first threshold value to 1 and setting values of the other pixels to 0. The system also performs the operation of applying a filter, to the plurality of pixels, wherein the filter responds to spatial frequencies of edges of white lines. The system also performs the operation of replacing a set value of a pixel with 0 if an absolute value of a filter response corresponding to the pixel is greater than or equal to a second threshold value and the set value of the pixel is 1. The system also performs the operation of extracting a line segment vector estimated to correspond to a crack by using a transform that estimates continuity of the plurality of pixels.

Another embodiment is directed toward a computer program product for detecting cracks from an object image comprising a computer readable storage device having a computer readable program stored therein.

The above summary is not intended to describe each illustrated embodiment or every implementation of the present disclosure.

DETAILED DESCRIPTION

An image analysis technique is provided in which, on the basis of an image obtained by applying a Gabor filter to a multiple resolution image, cracks in a road surface can be detected and distinguished from white lines and characters on the road surface.

As described herein, it is possible to solve the problems, which are drawbacks of the conventional techniques, in which visually detected cracks do not appear as edges and edges of white lines and characters on the road surface are detected as line segment vectors.

An objective of the present disclosure is to provide an image analysis method for quantifying cracks in a road surface from a road surface image recorded as a digital image, so as to quantify the degree of deterioration of the road surface.

According to various embodiments, definitions of terms are as follows:

Multiple resolution image: an image containing images with multiple scales obtained by scaling.

Multiple resolution analysis: a technique which involves applying a filter or orthogonal transform to a multiple resolution image for image analysis. The size of the base of the filter or orthogonal transform, instead of an image, may be scaled.

Figure 1:
FIG. 1 illustrates a road surface image in a first conventional technique.

FIG. 1 illustrates a road surface image in a first conventional technique.

The road surface image, which is an object image, is a picked-up image of an asphalt-paved road painted with white lines. The upward direction in FIG. 1 is the direction of travel of vehicles in the driving lane. White broken lines are painted as road markings on the asphalt-paved road. The area between the two white broken lines on the right and left sides is a vehicle lane. A part of a character (Japanese kanji character) appearing in the vehicle lane is a part of a road marking for indicating a traffic regulation, such as prohibition of overtaking. The road marking is vertically elongated and painted in white so that it can be read in the direction of travel of vehicles.

In the first conventional technique, cracks are visually quantified and recorded. Cracks with different rotational orientation components (8) appear in a scattering manner, because of their nature. Cracks may even extend into painted road marking portions (that is, the painted portions may be cracked).

Figure 2:
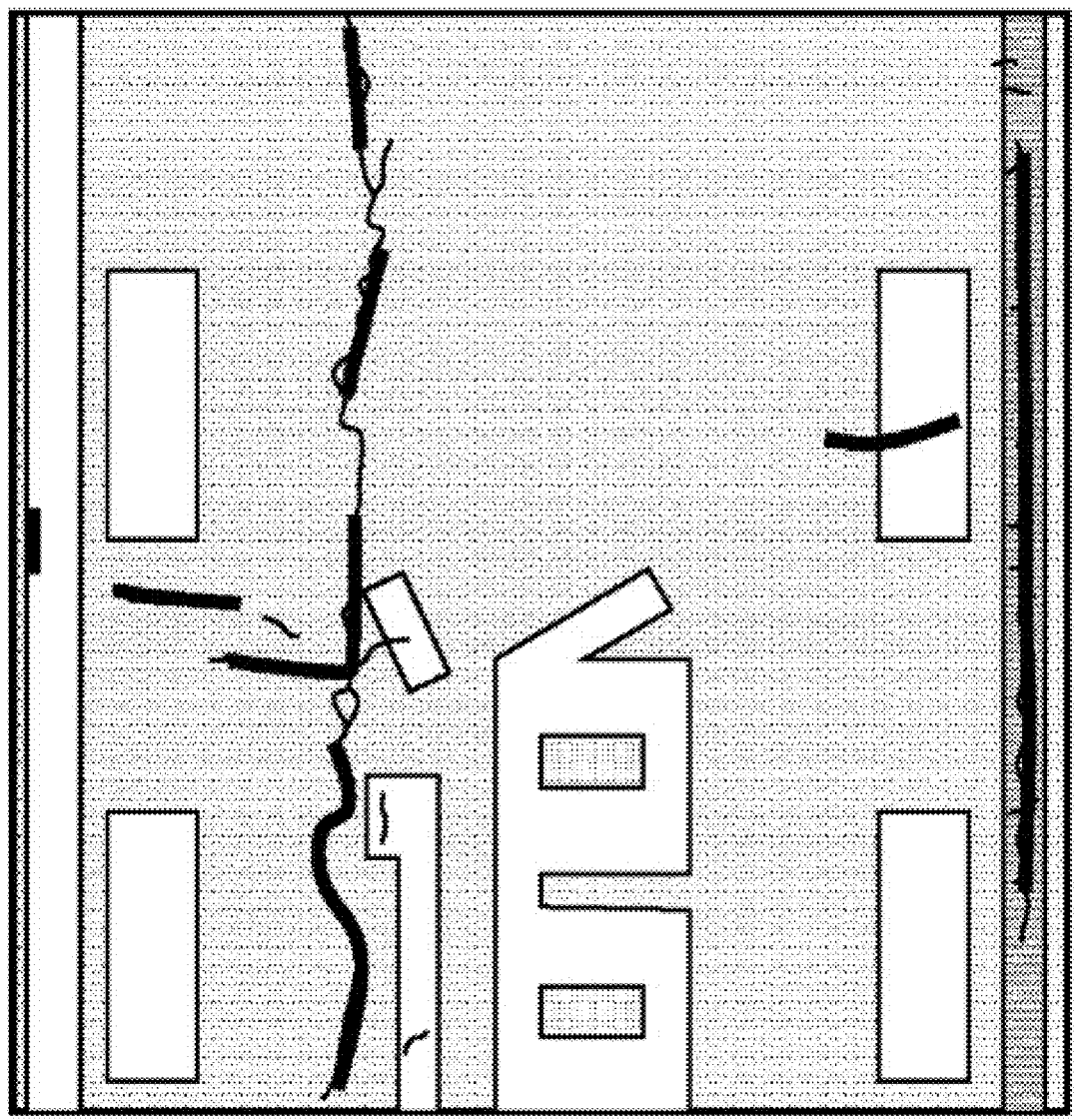
FIG. 2 illustrates visual quantification of cracks in the first conventional technique.

FIG. 2 illustrates visual quantification of cracks in the first conventional technique.

In FIG. 2, cracks are visually detected and marked with a plurality of line segments (thick lines).

Then, a coordinate pair of start and end points of each line segment vector is recorded. A problem with such a sensory inspection based on visual perception is that the criteria for determination of cracks and the way of drawing segment lines vary depending on the person who performs the inspection. Additionally, it is not realistic to visually process an entire image of a long and wide road.

Figure 3:
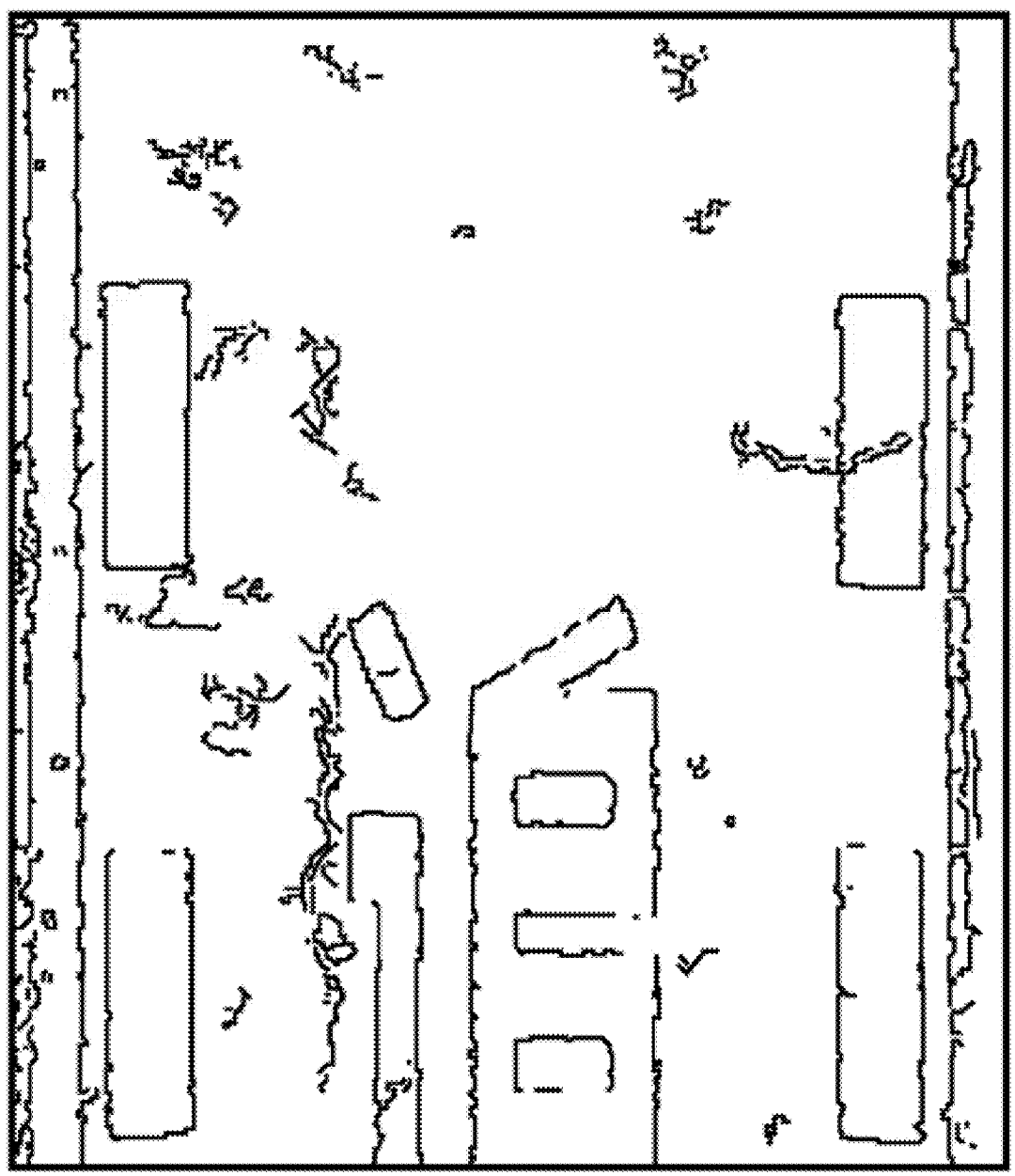
FIG. 3 illustrates crack detection using an edge detection algorithm in a second conventional technique.

FIG. 3 illustrates crack detection using an edge detection algorithm in a second conventional technique.

A technique, which will be generally devised by those skilled in the art is the use of an edge detection algorithm.

Of a plurality of edge detection algorithms that are known, an edge detection algorithm called Canny is used in FIG. 3. The Canny algorithm produces a relatively clear result of crack detection.

A result of edge detection is merely a set of pixel dot sequences corresponding to edges.

Figure 4:
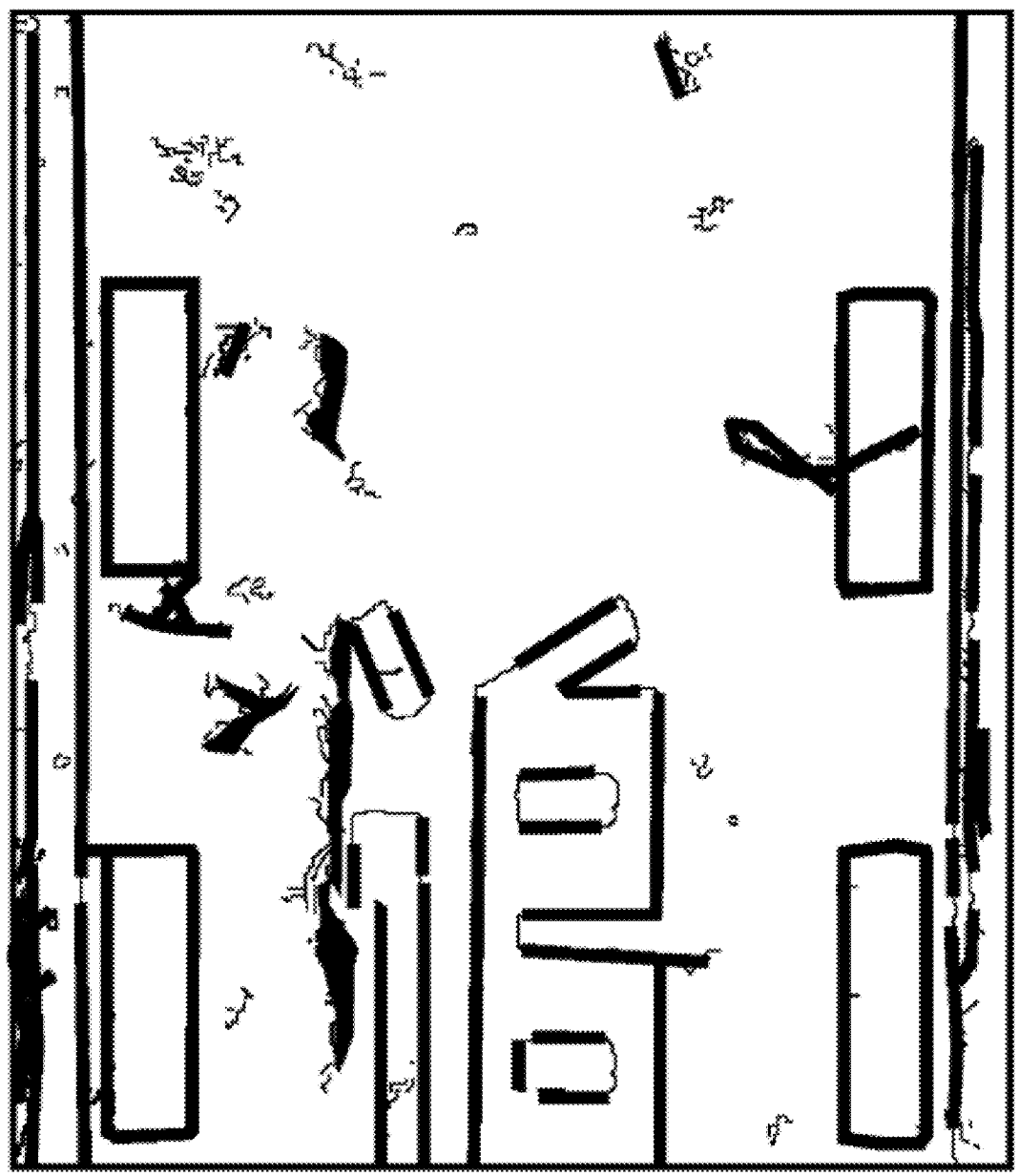
FIG. 4 illustrates extraction of line segment vectors in the second conventional technique.

FIG. 4 illustrates extraction of line segment vectors in the second conventional technique.

Since the result shown in FIG. 3 is merely a set of pixel dot sequences, linear components are extracted from the dot sequences by a Hough transform, and the resultant crack information is recorded as a set of line segment vectors.

A problem with this technique is that visually detected cracks may not appear as edges, or that the edges of white lines and character on the road surface may be detected as line segment vectors.

Japanese Patent Application Publication No. 2007-132858 describes a method for detecting flaws in the surface of a belt-like member having a pattern, such as a stripe pattern, or grooves. In this method, diagonal lines are detected by image processing.

Japanese Patent Application Publication No. 6-235626 describes a technique in which an inspection for scratches and the like in products is performed using image processing. This technique detects a unique pattern, such as a processing trace, on the surface of an object.

Japanese Patent Application Publication No. 2000-326494 describes a technique in which the surface of an object on a flat surface is inspected using image processing. The image processing involves using a low-pass filter to remove high spatial frequency components.

Japanese Patent Application Publication No. 2009-229085 describes an inspection device that generates an image in which flaws, such as scratches, are enhanced to detect flaws in an object to be inspected.

Japanese Patent Application Publication No. 2009-229085 also describes a technique in which "the brightness of each pixel in a flaw extracted image is inverted" and a Gabor filter is used as an orientation filter.

Japanese Patent Application Publication No. 9-61138 describes a technique for detecting cracks with high accuracy in a road surface inspection.

The technique described in Japanese Patent Application Publication No. 9-61138 is characterized in that images are cut out of an original road surface image and each of the cut-out images is binarized to extract edges of cracks and patching.

Japanese Patent Application Publication No. 2011-242365 describes a technique for detecting cracks in concrete from an image.

Japanese Patent Application Publication No. 2011-242365 also describes a technique in which, for detection of cracks, a plurality of edge filters are applied to a picked-up image of a concrete structure to compare pixel values.

The references cited, above, describe the technique for extracting edges of cracks or the like using image processing.

However, all the literatures only fragmentarily disclose components of the present application, and the techniques described in these literatures are not closely related to the present application.

Japanese Patent Application Publication No. 2004-145501, No. 2000-285236, and No. 2007-155405 are also cited, for reference purposes.

Figure 5:
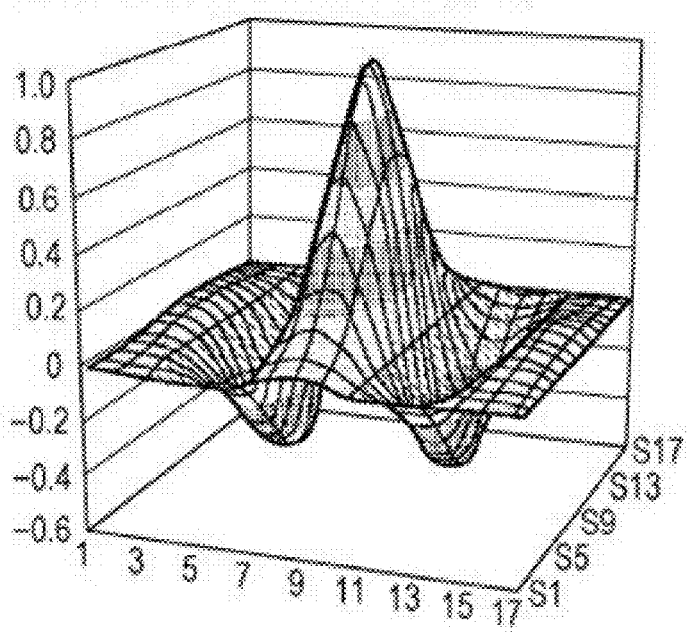
FIG. 5 is a diagram explaining a Gabor filter, according to various embodiments.
Figure 5:
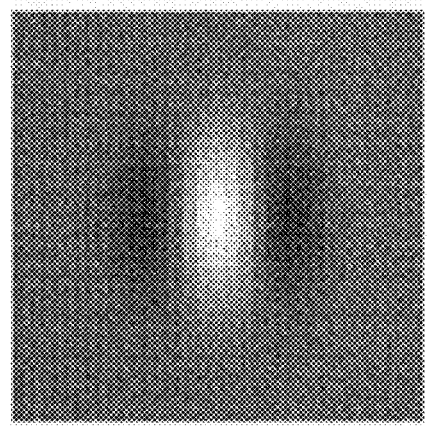

FIG. 5 is a diagram explaining a Gabor filter, according to various embodiments.

A two-dimensional Gabor filter can be expressed by equation (1).

When $\psi=0$, the shape of the Gabor filter is generally as shown in FIG. 5.

Visual cells having properties similar to those of Gabor filters are known to exist in the visual cortex of the human brain, and are considered to be capable of recognizing linear patterns.

Since each Gabor filter has an orientation, a plurality of Gabor filters are prepared to detect linear patterns with different orientations.

Figure 6:
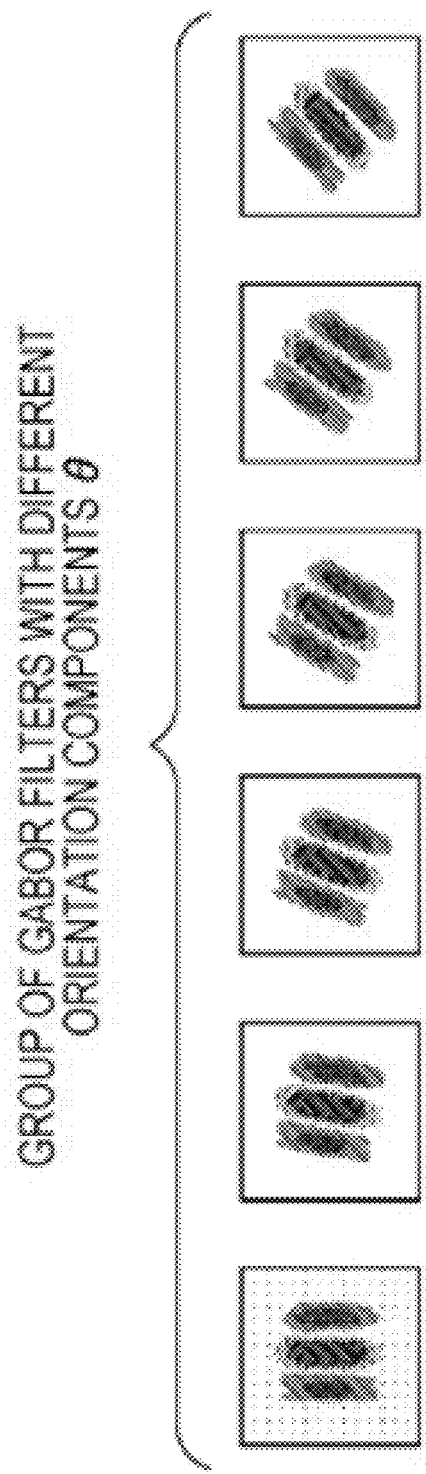
FIG. 6 illustrates a group of Gabor filters with different rotational orientation components, according to various embodiments.

FIG. 6 illustrates a group of Gabor filters with different rotational orientation components, according to various embodiments.

Since a Gabor filter responds to a specific spatial frequency band, it is preferable to select $\lambda$ responsive to line widths of cracks in equation (1).

According to Example 1, an image size is 500 by 500 pixels, and parameters in equation (1) are $\sigma=3.0$, $\gamma=0$, $\lambda=2\pi$, and $\psi=0$.

A group of twelve Gabor filters each corresponding to every $\pi/12$ of $\theta$ is designed, and each of the Gabor filters is applied to a grayscale inverted image to obtain a binary image, where pixels with responses greater than or equal to a first threshold value (Thd1=190) are set to 1 and the other pixels are set to 0.

Figure 7:
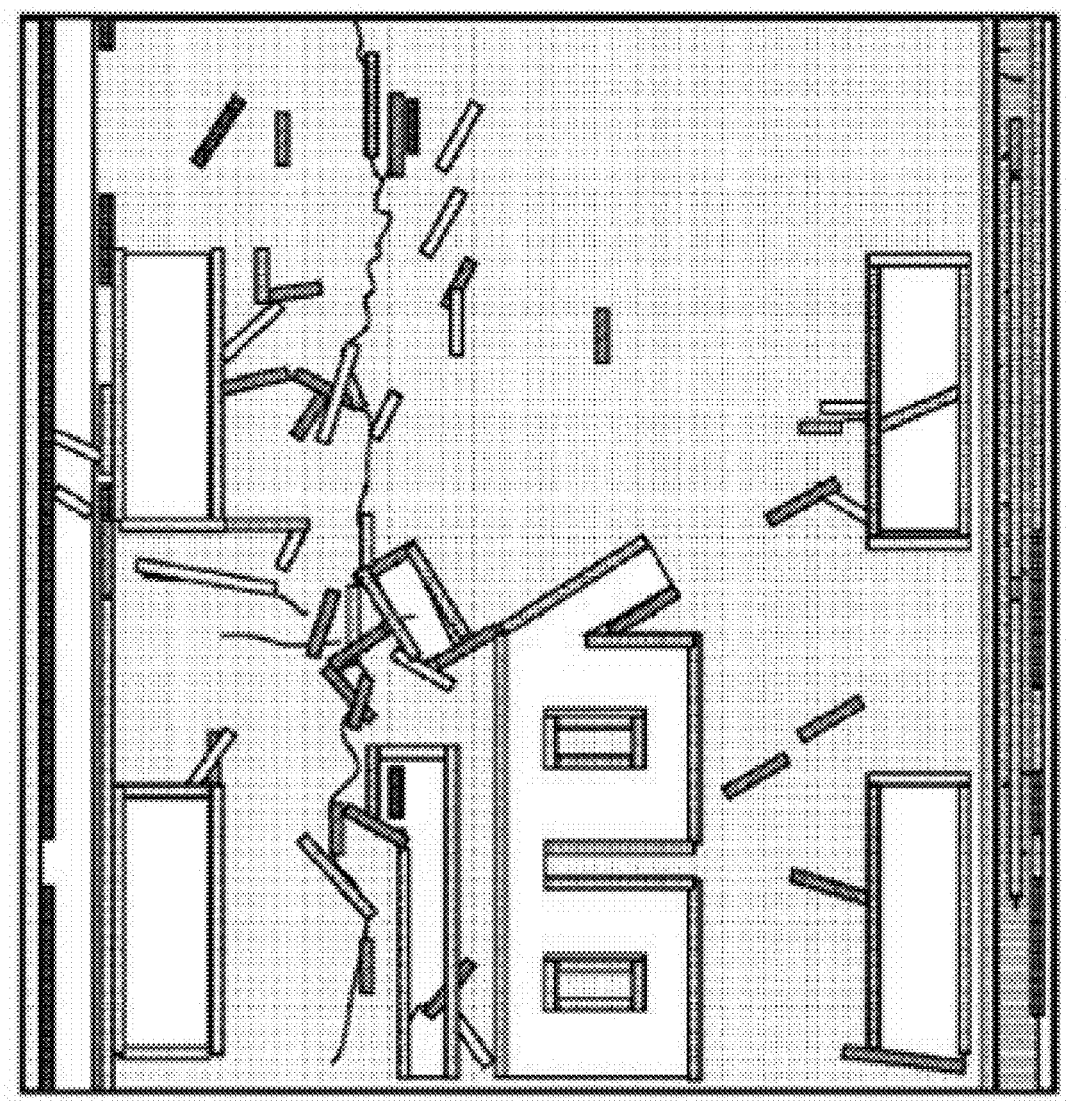
FIG. 7 illustrates line segment vectors detected by applying various techniques, according to various embodiments.

From this binary image, line segments are detected by a Hough transform to obtain line segment vectors, such as those illustrated in FIG. 7.

FIG. 7 illustrates line segment vectors detected by applying various techniques, according to various embodiments.

Differences in the type of screentone of line segments correspond to differences in the angular orientation $\theta$ of filters.

The reason for using a grayscale inverted image is that the filters in Example 1 give a positive response to a white linear pattern.

Major cracks are detected, but the edges of white lines and character are still detected as line segment vectors.

According to Example 2, filters with parameters different from those in Example 1 are designed to remove unnecessary line segment vectors.

A technical idea applied to principles in designing the filters is that although not responding to spatial frequencies of cracks, the filters respond to spatial frequencies of the edges of white lines and remove line segment vectors of the edges of the white lines and character from the group of line segment vectors in FIG. 7.

In Example 2, parameters in equation (1) are σ=7.5, λ=5π, and ψ=π/2.

The other parameters are the same as those in Example 1.

Figure 8:
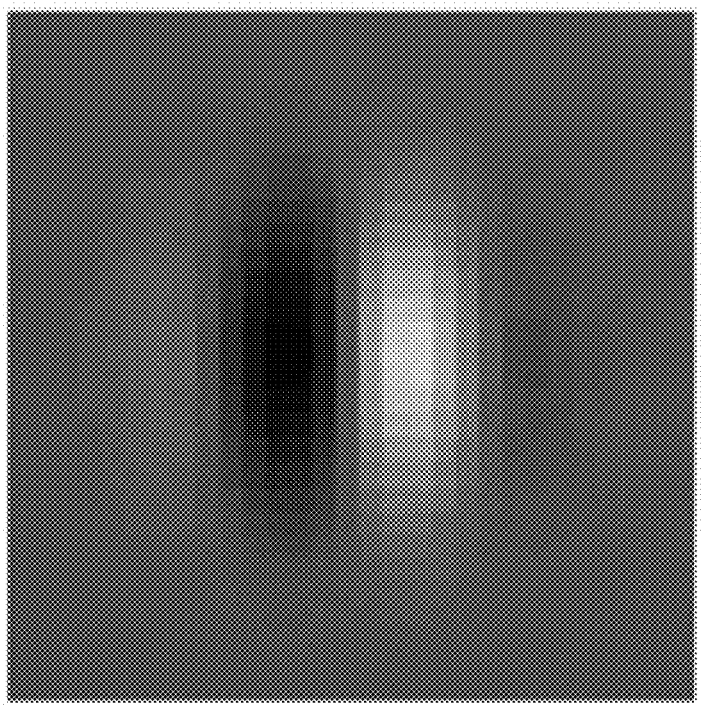
FIG. 8 shows a grayscale image of a filter to which an example technique is employed, according to various embodiments.

FIG. 8 shows a grayscale image of a filter to which an example technique is employed, according to various embodiments.

An image such as that in FIG. 8 is obtained when the filter is displayed as a grayscale image.

The filter gives a positive response at the boundary of a wide black region and a wide white region.

The absolute value of the filter response is determined. If the absolute value is greater than or equal to a second threshold value (Thd2=560) and the value of the corresponding pixel is 1 in the binary image of Example 1, the value of the pixel is replaced with 0.

This processing removes the edges of the white lines and character.

Figure 9:
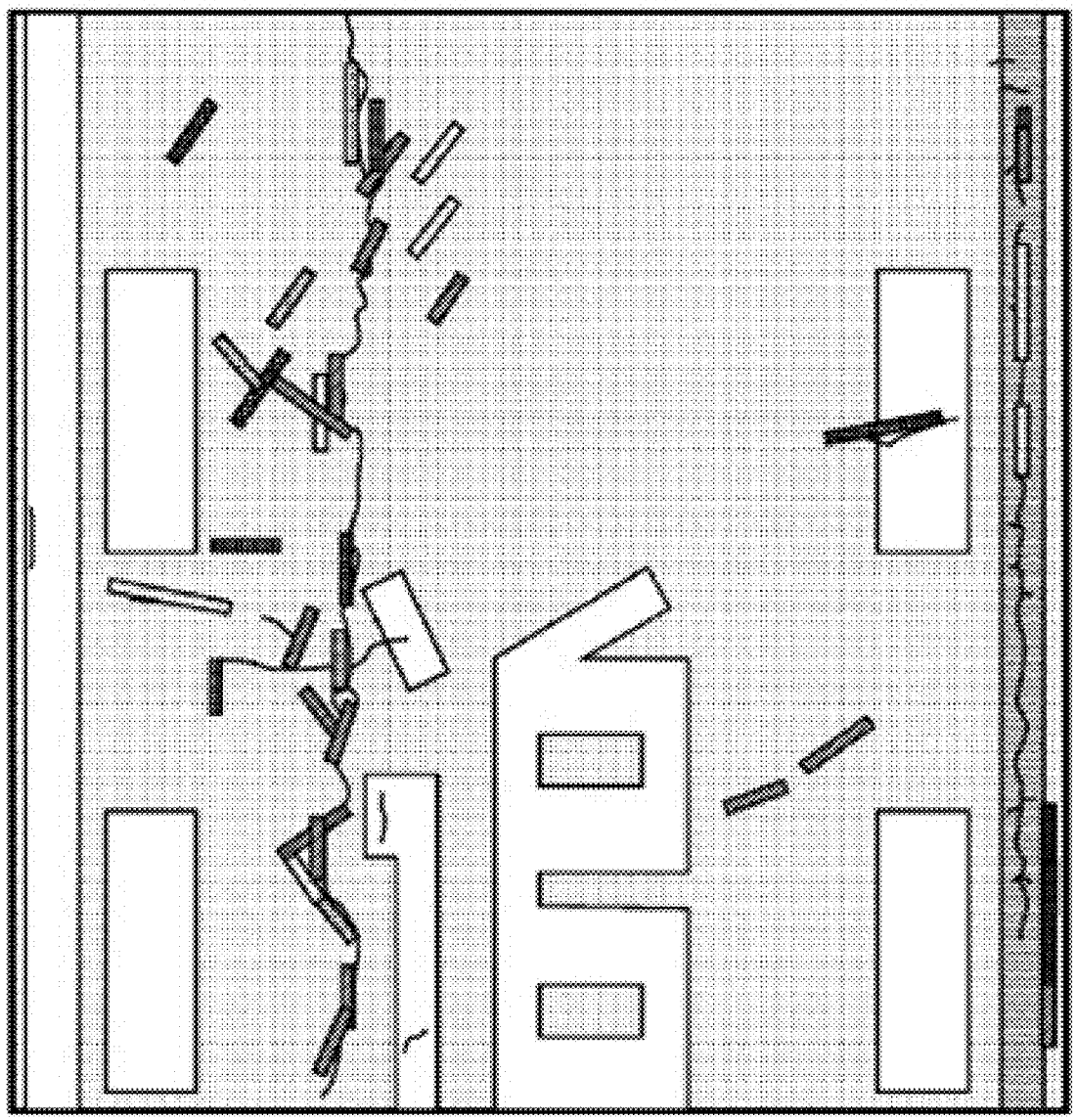
FIG. 9 illustrates line segment vectors obtained by applying an example technique, according to various embodiments.

Line segment vectors detected from the binary image by a Hough transform are shown in FIG. 9.

FIG. 9 illustrates line segment vectors obtained by applying an example technique, according to various embodiments.

The technique used here is not limited to the Hough transform. Any transform technique that estimates continuity of a plurality of pixels can be used.

FIG. 9 shows that edges of the white lines and character are removed.

The reason for determining the absolute value is to obtain a filter output that gives a positive response to both a black-white edge and a white-black edge.

A procedure of the present invention will now be described.

The following steps (Steps 1 to 5) detect cracks in a road surface, and remove the edges of white lines and character to obtain a group of line segment vectors of the cracks alone.

With this technique, cracks in the road surface can be detected and recorded by image processing.

Step 1: A grayscale inverted image is obtained by inverting the grayscale of an object image (the reason for this is that a filter in Step 2 gives a positive response to a white line segment pattern).

Step 2: Steps 3 to 5 are repeated while a rotation angle θ of the filter is varied.

Step 3: The filter in Example 1 is applied to the grayscale inverted image to obtain a binary image, in which values of pixels with filter responses greater than or equal to a given threshold value are 1 and values of the other pixels are 0.

Step 4: The filter in Example 2 is applied to the grayscale inverted image. Pixels corresponding to an absolute value greater than or equal to a given threshold value and having a pixel value of 1 in the binary image of Example 1 are replaced with 0 (that is, the edges of the white line and character are removed).

Step 5: Line segment vectors are extracted from the resultant binary image by a Hough transform and recorded.

The technical idea of the present invention can be embodied as a method to be executed by a computer.

In embodying the present invention, the region of an object image is divided into a plurality of pixels for digitization.

A multiple resolution image can be obtained as an image that contains images with multiple scales obtained by scaling.

It is obvious that the technical idea of the present invention can also be embodied as a system to be executed by a computer, or as a program to be executed by a computer.

What is claimed is:

1. A method for detecting cracks from an object image, the method comprising the steps of:
    dividing a region of the object image into a plurality of pixels;
    inverting a grayscale value of each of the plurality of pixels;
    preparing a group of filters with different rotational orientation components and applying one of the filters to the plurality of pixels;
    setting values of pixels with filter responses greater than or equal to a first threshold value to 1 and setting values of the other pixels to 0;
    applying a filter, to the plurality of pixels, wherein the filter responds to spatial frequencies of edges of white lines;
    replacing a set value of a pixel with 0 if an absolute value of a filter response corresponding to the pixel is greater than or equal to a second threshold value and the set value of the pixel is 1; and
    extracting a line segment vector estimated to correspond to a crack by using a transform that estimates continuity of the plurality of pixels.

2. The method of claim 1, wherein the group of filters is a group of Gabor filters.

3. The method of claim 2, wherein the method is repeated for each of the Gabor filters of the group of Gabor filters.

4. The method of claim 1, wherein the group of filters having different rotational orientation components have λ selected to be responsive to line widths of cracks.

5. The method of claim 1, wherein the steps are applied to more than one filter in the group of filters having different rotational orientation components.

6. The method of claim 1, wherein the edges of white lines; include edges of white road markings.

7. The method of claim 1, wherein the transform that estimates continuity of the plurality of pixels is a Hough transform.

8. A system for detecting cracks from an object image by being executed on a computer, the system performing the operations of:
    dividing a region of the object image into a plurality of pixels;
    inverting a grayscale value of each of the plurality of pixels;
    preparing a group of filters with different rotational orientation components and applying one of the filters to the plurality of pixels;
    setting values of pixels with filter responses greater than or equal to a first threshold value to 1 and setting values of the other pixels to 0;
    applying a filter, to the plurality of pixels, wherein the filter responds to spatial frequencies of edges of white lines;
    replacing a set value of a pixel with 0 if an absolute value of a filter response corresponding to the pixel is greater than or equal to a second threshold value and the set value of the pixel is 1; and
    extracting a line segment vector estimated to correspond to a crack by using a transform that estimates continuity of the plurality of pixels.

9. The system of claim 8, wherein the group of filters is a group of Gabor filters.

10. The system of claim 9, wherein the system repeats performing the operations for each of the Gabor filters of the group of Gabor filters.

11. The system of claim 8, wherein the group of filters having different rotational orientation components have λ selected to be responsive to line widths of cracks.

12. The system of claim 8, wherein the steps are applied to more than one filter in the group of filters having different rotational orientation components.

13. The system of claim 8, wherein the edges of white lines include edges of white road markings.

14. The system of claim 8, wherein the transform that estimates continuity of the plurality of pixels is a Hough transform.

15. A computer program product for detecting cracks from an object image comprising a computer readable storage device having a computer readable program stored therein, wherein the computer readable program, when executed on a computing device, causes the computing device to:

divide a region of the object image into a plurality of pixels;

invert a grayscale value of each of the plurality of pixels;

prepare a group of filters with different rotational orientation components and applying one of the filters to the plurality of pixels;

set values of pixels with filter responses greater than or equal to a first threshold value to 1 and setting values of the other pixels to 0;

apply a filter, to the plurality of pixels, wherein the filter responds to spatial frequencies of edges of white lines;

replace a set value of a pixel with 0 if an absolute value of a filter response corresponding to the pixel is greater than or equal to a second threshold value and the set value of the pixel is 1; and extract a line segment vector estimated to correspond to a crack by using a transform that estimates continuity of the plurality of pixels.

16. The computer program product of claim 15, wherein the group of filters is a group of Gabor filters.

17. The computer program product of claim 16, wherein the computing device is further configured to repeat performing the operations for each of the Gabor filters of the group of Gabor filters.

18. The computer program product of claim 15, wherein the group of filters having different rotational orientation components have λ selected to be responsive to line widths of cracks.

19. The computer program product of claim 15, wherein the steps are applied to more than one filter in the group of filters having different rotational orientation components.

20. The computer program product of claim 15, wherein the transform that estimates continuity of the plurality of pixels is a Hough transform.

* * * * *